United States Patent [19]

Sholder et al.

[11] Patent Number: 4,989,602
[45] Date of Patent: Feb. 5, 1991

[54] PROGRAMMABLE AUTOMATIC IMPLANTABLE CARDIOVERTER/DEFIBRILLATOR AND PACEMAKER SYSTEM

[75] Inventors: Jason A. Sholder, Northridge; Brian M. Mann, Los Angeles, both of Calif.

[73] Assignee: Siemens-Pacesetter, Inc., Sylmar, Calif.

[21] Appl. No.: 336,996

[22] Filed: Apr. 12, 1989

[51] Int. Cl.$^5$ .............................................. A61N 1/39
[52] U.S. Cl. ......................... 128/419 D; 128/419 PG
[58] Field of Search ........ 128/419 D, 419 P, 419 PG, 128/419 R

[56] References Cited

U.S. PATENT DOCUMENTS

| Re. 27,757 | 9/1973 | Mirowski | 128/419 |
|---|---|---|---|
| 3,857,398 | 12/1974 | Rubin | 128/419 |
| 4,088,140 | 5/1978 | Rockland et al. | 128/419 |
| 4,114,628 | 9/1978 | Rizk | 128/419 |
| 4,181,133 | 1/1980 | Kolenik et al. | 128/419 |
| 4,300,567 | 11/1981 | Kolenik et al. | 128/419 D |
| 4,693,253 | 9/1987 | Adams | 128/419 |
| 4,712,555 | 12/1987 | Thornander et al. | 128/419 PG |
| 4,787,389 | 11/1988 | Tarjan | 128/419 PG |
| 4,788,980 | 12/1988 | Mann et al. | 128/419 PG |
| 4,827,936 | 5/1989 | Pless et al. | 128/419 |
| 4,830,006 | 5/1989 | Haluska et al. | 128/419 |

Primary Examiner—Lee S. Cohen
Assistant Examiner—Kennedy J. Schaetzle
Attorney, Agent, or Firm—Bryant R. Gold; Leslie S. Miller; Lisa P. Weinberg

[57] ABSTRACT

A non-programmable automatic implantable cardioverter/defibrillator (AICD) capable of providing programmable thresholds for triggering high energy stimulation pulse(s) from the AICD is coupled to an implantable programmable pacemaker which preferably includes bradycardia support and/or tachycardia support using low enery output pulses. When the low energy antitachycardia pulse(s) from the pacemaker fail to terminate a tachycardia, or whenever other various thresholds, as sensed by programmable sensing circuits of the pacemaker, are exceeded, the high enery pulses from the AICD may be selectively invoked by an AICD trigger circuit included within the pacemaker. Coupling between the AICD and pacemaker is by either a direct electrical connection, or by an indirect connection, such as through the use of narrow pulse sequences generated by the pacemaker which are of insufficient energy to invoke a cardiac response but are of sufficient energy to be sensed by the AICD sensing circuits.

20 Claims, 4 Drawing Sheets

PROGRAMMABLE AUTOMATIC IMPLANTABLE CARDIOVERTER/DEFIBRILLATOR AND PACEMAKER SYSTEM

BACKGROUND OF THE INVENTION

Field of the Invention

The present invention relates generally to automatic implantable cardioverter/defibrillators and implantable programmable pacemakers, and more particularly to a system which combines a non-programmable automatic implantable cardioverter/defibrillator with an implantable programmable pacemaker in a way which allows the pacemaker to programmably control, at least in part, the operation of the otherwise non-programmable cardioverter/ defibrillator.

An automatic implantable cardioverter/defibrillator (hereafter "AICD") provides one or more high energy stimulation pulses to a heart when: (1) the AICD senses that the heart is beating too fast (tachycardia); or (2) the AICD senses that the heart is not beating at all (fibrillation). In the case of a tachycardia, the delivery of the high energy stimulation pulse or pulses is usually referred to as "cardioversion", and the stimulus is delivered in synchrony with the heart's QRS wave. This synchronization is done to avoid stimulating the heart during the T-wave portion of the P-QRS-T cardiac cycle.

In the case of fibrillation, the heart has stopped so there is no QRS complex. Hence, there is no need to synchronize the delivered high energy stimulation pulse or pulses with any cardiac event. The purpose of delivering the high energy stimulation pulse or pulses to the heart is, of course, to shock the heart back into beating at a more normal rate, i.e., to break the tachycardia, or to defibrillate the fibrillating heart. The high energy stimulation pulses generated by the AICD are commonly referred to as either "cardioversion" pulses or "defibrillation" pulses.

Conventional AICD devices known in the art typically include a built-in sensor circuit for sensing, through attached sensing electrodes, the rate at which the heart is beating. If the sensed heart rate exceeds a high fixed rate threshold, the AICD is triggered to deliver a cardioversion pulse to the heart through separate stimulating electrodes. If the sensed heart rate is less than a low fixed rate threshold, the AICD is triggered to deliver a defibrillation pulse to the heart through the stimulating electrodes. By using fixed, non-programmable, rate thresholds in this fashion, the sensing and stimulating circuits of the AICD device may be kept simple and compact.

The doctor or physician who is implanting an AICD device must determine the correct high and low fixed rate thresholds which are needed for the particular patient. Typically, only the high rate threshold is of concern, because the low rate threshold is usually just a long escape interval which must time out without any cardiac activity being sensed. However, for some patients exhibiting bradycardia, even the low rate threshold must be carefully selected.

Once the correct thresholds are determined, the doctor must obtain an AICD device which has the desired thresholds built-in to its design. Unfortunately, this requires that the AICD device be specially ordered from a manufacturer, or that the implanting doctor maintain a large inventory of AICD devices covering a wide threshold range. Further, after implant, there is some likelihood that the correct high rate threshold for the patient may change, particularly if the patient is taking prescribed medication (drugs). Hence, there is a need in the art for a programmable AICD device wherein the high and low rate thresholds may be readily modified.

Moreover, in view of the already existing AICD devices having fixed high and low rate thresholds, there is an immediate need in the art for a programmable means or system for modifying, as required, the fixed rate thresholds associated with these devices. The present invention advantageously addresses these and other needs. It is also an objective that all of the aforesaid advantages and objectives be achieved without incurring any substantial relative disadvantage.

SUMMARY OF THE INVENTION

The disadvantages and limitations of the background art discussed above are overcome by the present invention. With this invention, an implantable programmable pacemaker device is combined with a fixed rate AICD device in a manner which allows the fixed-rate thresholds of the AICD device to be replaced with the programmable thresholds included within the pacemaker device.

More particularly, the present invention combines an implantable programmable pacemaker, preferably one which includes means for recognizing and treating bradycardia and/or tachycardia conditions using low energy output pulses, with an otherwise conventional AICD. This enables the combined unit to trigger the desired high energy stimulation pulse or pulses from the AICD whenever the low energy antitachycardia or other stimulation pulses from the pacemaker fail to terminate a tachycardia or bradycardia condition, and whenever various other thresholds, as sensed by the programmable sensing circuits of the pacemaker, are exceeded.

Stated somewhat differently, it is a feature of the present invention to allow the versatility and flexibility of a modern programmable pacemaker, especially its versatility in sensing and responding to various cardiac activities, to be used with an otherwise conventional and inflexible AICD device. This results in an extremely versatile pacing/stimulating system which is capable of providing one or more high energy stimulation pulses as required based on programmable threshold values.

Thus, the present invention may be characterized as a programmable cardioverter/defibrillator system including three basic elements. The first of these elements is an automatic implantable cardioverter/ defibrillator (AICD), with the AICD including high/low rate sensing means for sensing when a heart is beating above a fixed high threshold rate or below a fixed low threshold rate, and means for delivering a high energy cardioversion/defibrillation pulse to the heart whenever the high/low rate sensing means senses that the heart is beating above the fixed high threshold rate or below the fixed low threshold rate.

The second of the three elements is an implantable programmable pacemaker, with the pacemaker including heart-rate sensing means for sensing the rate at which the heart is beating, means for processing the sensed heart rate to determine whether the sensed heart rate lies within a programmed range of acceptable heart rates, and programming means for allowing a programmed range of acceptable heart rates to be programmed into the processing means.

The third element is a coupling means for coupling the operation of the AICD to the pacemaker, with the coupling means including means for triggering the generation of the cardioversion/defibrillation pulse from the AICD whenever the heart rate sensed by the heart-rate sensing means of the pacemaker does not fall within the prescribed range of acceptable heart rates. This combination allows the fixed high and low threshold rates of the AICD to be replaced by the programmed range of heart rates of the implantable programmable pacemaker.

In a first embodiment of the invention, the coupling means which couples the operation of the AICD to the pacemaker is a direct electrical connection. In accordance with this first embodiment, the circuits of the pacemaker are modified to include an AICD trigger circuit. A sensing electrode of an otherwise conventional ACID is then directly connected to an available connection point at the output connector of the pacemaker. The trigger circuit provides appropriate trigger signals to the connection point at the pacemaker's output connector where the AICD's sensing electrode is connected. These trigger signals, or the lack thereof, are sensed by the sense circuits of the AICD, thereby causing the AICD to generate the appropriate high energy stimulation pulse(s).

The AICD trigger circuit included within the pacemaker is a rate threshold circuit which may be programmed in the same manner as are other parameters of the pacemaker. That is, when the conventional sensing circuits of the pacemaker sense that the heart rate falls within a programmed range of acceptable heart rate values, an appropriate signal is sent to the AICD device through its sensing electrode that the heart rate is acceptable and that no high energy stimulation pulses are needed.

However, when the pacemaker senses that the heart rate does not fall within a programmed range of acceptable heart rates, that is, the sensed heart rate is either too fast or too slow as compared to programmed high and low values, an appropriate trigger signal is sent to the AICD device, over the direct electrical connection, in order to evoke the desired response, namely one or more high energy stimulation pulses from the AICD. In this manner, the otherwise conventional AICD device having a fixed rate threshold is converted to an AICD device having a programmable threshold.

In a second embodiment of the invention, an indirect electrical connection is made between the pacemaker device and the AICD device. In accordance with this second embodiment, the sense amplifier of the AICD device is coupled to the pacemaker through the use of low energy (typically narrow) pulse sequences transmitted to the heart by the pacemaker through the pacemaker's normal stimulation mechanism. These low energy pulse sequences do not have enough energy associated with them to stimulate the heart, but they do have sufficient energy to be sensed by the sensing electrode and sense circuit of the AICD device, and are designed to be interpreted by the AICD sense circuit as cardiac activity.

Preferably, different sequences of such narrow, non-stimulating pulses are programmed into the pacemaker and are used to signal the AICD that different events have been sensed, such as the occurrence of a tachycardia, a bradycardia or a fibrillation condition. The sense circuits within the AICD device are modified as required in order to discriminate between the different sequences of pulses, and an appropriate response is evoked depending upon the condition which is signaled.

For example, if a fibrillation condition is sensed by the pacemaker and signaled to the AICD device through the generation of a particular sequence of narrow, non-stimulating pulses, the AICD device may respond by delivering a sequence of very high energy stimulation pulses in an attempt to defibrillate the heart. In contrast, if a tachycardia condition is sensed by the pacemaker and signaled to the AICD device through the generation of a different sequence of narrow, non-stimulating pulses, the AICD device may respond by delivering a single high energy stimulation pulse.

This second embodiment of the invention may thus be described as a programmable implantable medical system designed to deliver one or more high energy stimulation pulses to a heart whenever the heart rate exceeds programmable threshold rate values. This system includes in its AICD portion an AICD device having sensing means for sensing when the heart rate is above a fixed high threshold rate value, and/or below a fixed low threshold rate value. The AICD portion of the device also includes means for delivering a high energy stimulation pulse to the heart whenever the sensing means senses that the heart rate exceeds the fixed high threshold rate value or is less than the fixed low threshold rate value.

The system includes in its pacemaker portion an implantable pacemaker device having four elements. These elements are a sensing means for sensing the heart rate, a programming means for programming the specified range of rates into the processing means, a means for processing or monitoring the sensed heart rate to determine when it does not fall within the specified range of heart rates, and a means for sending a pulse sequence of low energy pulse(s) to the heart in response to a determination by the processing means that the heart rate does not fall within the specified range of heart rates.

The low energy pulse sequences sent by the pacemaker must have an energy level sufficient to be detected by the AICD sensing means, but insufficient to stimulate the heart. Hence, the low energy pulse sequences are detected by the AICD sensing means and are interpreted as a heart rate which exceeds the fixed high threshold rate of the AICD, whereupon the delivery means of the AICD device delivers the ordered high energy stimulation pulse or pulses to the heart.

Alternatively, the present invention in either embodiment may be viewed as the combination of an AICD device and an implantable programmable pacemaker device. The AICD device includes a first sensing means for sensing when a heart is beating above a fixed high threshold rate or below a fixed low threshold rate, and means for delivering one or more high energy stimulation pulses to the heart whenever the first sensing means senses that the heart is beating above the fixed high threshold rate or below the fixed low threshold rate. The pacemaker device includes a second sensing means for sensing the rate at which the heart is beating, a programming means for allowing a range of heart rates to be programmed into the processing means, and a means for processing the sensed heart rate to determine whether it falls within the programmed range of acceptable heart rates.

This combination further includes a signaling means within the pacemaker device for sending a trigger signal to the AICD device, and a receiving means within the AICD device for receiving the trigger signal and for initiating the delivery of one or more high energy stimulation pulses to the heart in response to receiving the trigger signal. In one embodiment of the invention, the AICD device may be a conventional AICD device having a sensing electrode. In this case, the signaling means of the pacemaker is the trigger circuit previously described, and the receiving means of the AICD is simply the sensing electrode of the AICD device connected to the output of the pacemaker trigger circuit.

Further, the present invention includes a method of converting the fixed high or low rate threshold values of an AICD device to programmable high or low rate threshold values. The AICD device used in this method includes means for generating one or more high energy cardioversion/defibrillation pulses whenever the heart rate sensed by the sensing means within the AICD device either exceeds the fixed high rate threshold value or is less than the fixed low rate threshold value.

The method includes two steps, with the pacemaker including a heart rate sensing means for sensing when the heart rate exceeds a programmable upper limit or is less than a programmable lower limit. The first step is coupling the programmable pacemaker to the AICD device. The second step is triggering the generation of one or more high energy cardioversion/defibrillation pulses whenever the heart rate sensing means of the pacemaker senses a rate which exceeds the programmable upper limit or is less than the programmable lower limit.

The present invention also includes a method of combining the operation of a non-programmable AICD with the operation of an implantable programmable pacemaker. The AICD used with this method includes means for sensing a first heart rate condition wherein the sensed heart rate exceeds a fixed upper rate value, and for sensing a second heart rate condition wherein the sensed heart rate is less than a fixed lower rate value. The first heart rate condition is deemed a tachycardia condition wherein the heart rate is too fast, and the second heart rate condition is deemed either a bradycardia condition wherein the heart rate is too slow or a fibrillation condition wherein the heart has stopped.

The AICD further includes means for generating one or more high energy cardioversion/defibrillation pulses which are automatically delivered to the heart in response to the sensing of either the first or second heart condition. The pacemaker used with this method includes means for sensing whether the heart rate exceeds programmable high or low rate threshold values, and means for delivering controlled energy stimulation pulses to the heart at specified times in order to maintain the heart rate at a programmed rate.

The method of combining the operation of the AICD and the pacemaker includes four steps. The first of these steps is programming a desired rate threshold value or values into the pacemaker. The second step is monitoring the heart rate to determine if the rate threshold value or values are exceeded. The third step is, in response to a determination in the second step that the heart rate has exceeded the rate threshold value or values, sending a trigger signal to the AICD from the pacemaker. Finally, the fourth step is generating the high energy cardioversion/defibrillation pulse or pulses in response to receiving the trigger signal sent in the third step.

DESCRIPTION OF THE DRAWINGS

These and other advantages of the present invention are best understood with reference to the drawings, in which.

DETAILED DESCRIPTION OF THE PREFERRED EMBODIMENT

The preferred embodiment of the present invention is described in the following description. This description is not to be taken in a limiting sense but is made merely for the purpose of describing the general principles of the invention. The scope of the invention should be ascertained with reference to the appended claims.

Figure 1:
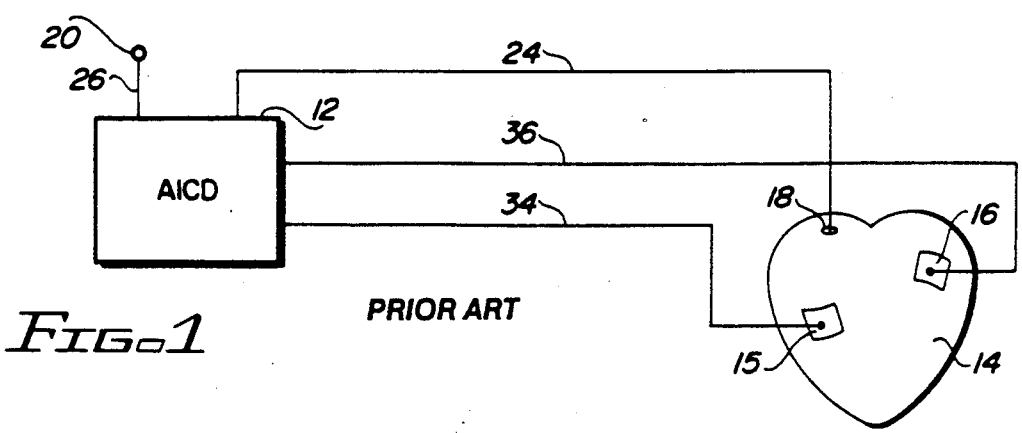
FIG. 1 is a previously known AICD with patch electrodes and sensing electrodes connected to a heart.

Before describing the present invention, it may be helpful to review the basic operation of a conventional AICD device and a conventional programmable pacemaker. Accordingly, reference is first made to FIGS. 1–3 where these devices are illustrated. In FIG. 1, for example, a diagram showing an implanted AICD 12 connected to a heart 14 is shown schematically. Typically, the AICD 12 includes separate stimulating electrodes 15 and 16, and sensing electrodes 18 and 20. The stimulating electrodes 15 and 16 are typically large area electrodes which are in physical contact with the exterior of the heart 14. Often, these electrodes are referred to in the art as "patch electrodes." Other types of cardioversion or defibrillation electrodes, including deployable electrodes which make contact with the inside or outside of the heart, could also be used.

The sensing electrodes 18 and 20 are shown in FIG. 1 as being separate from the stimulating electrodes 15 and 16. However, it will be understood by those skilled in the art that, as is common in pacemaker art, the sensing electrodes could be the same as the stimulating electrodes. In this case the AICD 12 would include an appropriate multi-pole isolation switch (not shown) at its output to isolate the sense circuits of the AICD 12 from the stimulating circuits.

As shown in FIG. 1, one sensing electrode 18 is in contact with the heart 14. The other sensing electrode 20, typically referred to as the return electrode, is positioned near the AICD 12. This is a unipolar configuration, and the electrical path between the two sensing electrodes 18 and 20 is by way of body fluids. In practice, the return electrode 20 may be part of the case of the AICD 12. Of course, a bipolar sensing electrode configuration could also be employed wherein both electrodes 18 and 20 are positioned near the desired tissue location where heart activity is being sensed. Unipolar and bipolar sensing electrode configurations are well known and are described in the art.

Figure 2:
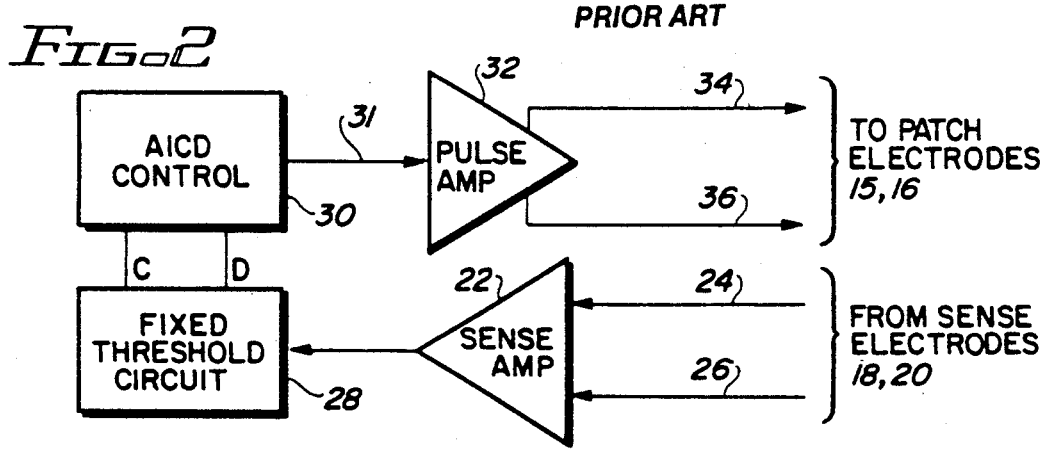
FIG. 2 is a functional block diagram of the AICD of FIG. 1.

Referring next to FIG. 2, a functional block diagram of the AICD 12 of FIG. 1 is shown. As seen from this figure, the AICD includes a sense amplifier 22 connected to the leads 24 and 26 which are connected to the sense electrodes 18 and 20 respectively. The output of the sense amplifier 22 is directed to a fixed threshold circuit 28. The function of the fixed threshold circuit 28 is to determine if the sensed heart rate exceeds a fixed upper rate limit, or is less than a fixed lower rate limit.

If the sensed heart rate exceeds a fixed upper rate limit, a trigger signal "C" is generated, indicating that one or more cardioversion high energy stimulation pulses are needed. If the sensed heart rate is less than a fixed lower rate limit, a trigger signal "D" is generated indicating that one or more defibrillation high energy stimulation pulses are needed. For a simple AICD device, the "C" and "D" trigger signals will be the same, and the same high energy stimulation pulses are generated regardless of whether a tachycardia or a bradycardia/ fibrillation condition is sensed. More sophisticated AICD devices will distinguish between the heart condition and deliver a particular type or pattern of high energy stimulation pulses depending upon the heart condition which is sensed.

The fixed threshold circuits 28 are typically realized using a simple oscillator (clock) and a counter circuit which determines whether a heart beat is sensed within a prescribed interval of time (to determine whether the heart is beating at least at a minimum rate below which a bradycardia or fibrillation condition exists), and if so, how much time has elapsed since the last heart beat was sensed (to determine the period of the heart rate, which determination indicates whether an upper heart rate limit has been exceeded). Alternatively, simple capacitive charging circuits used in conjunction with analog threshold circuits may be used to perform this timing function. Such timing and measuring circuits are well known in the art.

Still referring to FIG. 2, it may be seen that the "C" and "D" trigger signals are directed to an AICD control circuit 30. For simple AICD devices, the AICD control circuit 30 may be nothing more than an OR gate or wire which directs the appropriate "C" and/or "D" trigger signals to the pulse amplifier 32. More sophisticated AICD devices may include means within the AICD control circuit 30 for generating a desired pattern and or frequency of low level trigger signals which may be sent to the output pulse amplifier 32 depending upon whether the "C" or "D" trigger signals are received.

The low level trigger signal(s) from the AICD control circuit 30 is received by the pulse amplifier 32 over a signal line 31. The purpose of the pulse amplifier 32 is simply to convert the low level trigger signals received from the AICD control circuit 30 into a high energy stimulation pulse which may be delivered to the stimulating electrodes 15 and 16 (FIG. 1) over two conductive paths 34 and 36. In practice, such a circuit may simply be a large capacitor with appropriate charging paths and circuits so that the capacitor may be charged to a large voltage level and, upon receipt of the trigger signal, be discharged through the conductive paths 34 and 36 to the stimulating electrodes 15 and 16.

It should be understood that the above description of the AICD 12 discussed in conjunction with FIGS. 1 and 2 is functional in nature, and that numerous variations exist in the art relative to the actual circuits and techniques employed for achieving the desired stimulation of the heart in the event a prescribed heart condition warranting a high energy stimulation pulse(s) is sensed.

Figure 3:
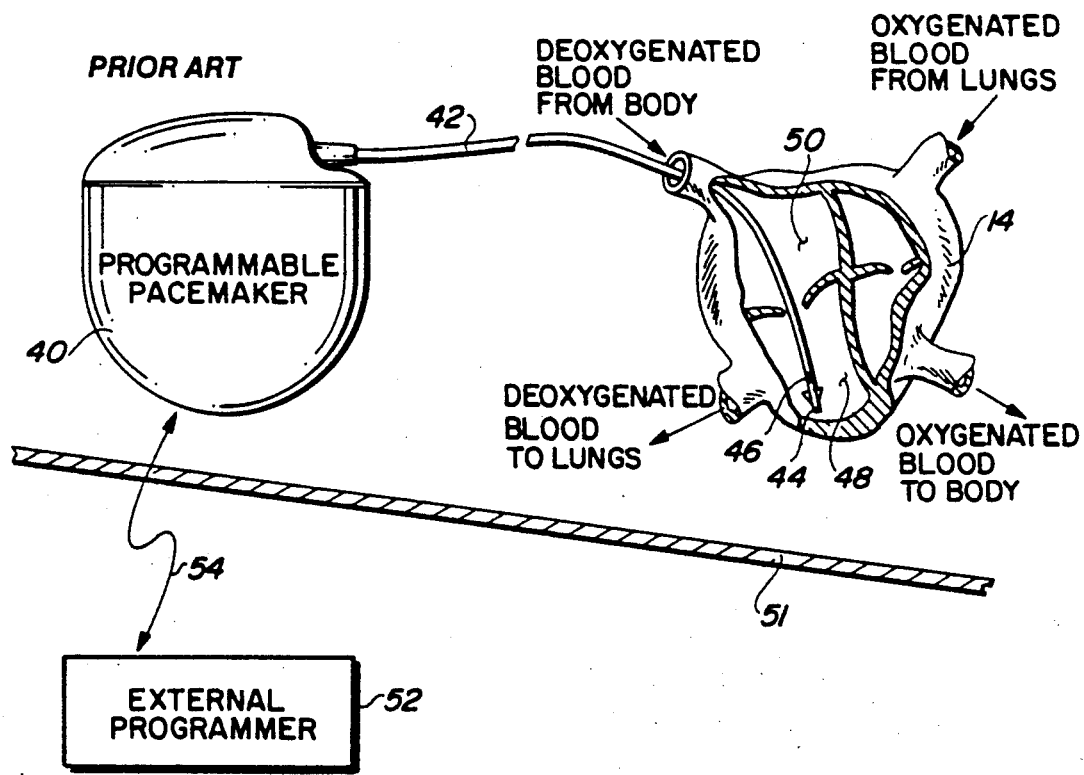
FIG. 3 shows a previously known programmable implantable pacemaker, including the external programmer used to program the pacemaker.

Referring next to FIG. 3, a pictorial diagram of a conventional programmable pacemaker 40 is illustrated, along with the heart 14 to which the pacemaker 40 is connected by means of a suitable bipolar stimulation lead 42. The bipolar stimulation lead 42 includes a tip electrode 44 in contact with the inside of the right ventricle 48 (one of the four chambers of the heart 14). A ring electrode 46 is spaced a short distance away from the tip electrode 44. Cardiac activity occurring within the right ventricle 48 is sensed through the tip electrode 44/ring electrode 46 combination, and low level stimulation pulses are delivered to the right ventricle 48 from the pacemaker 40, on demand, through this same electrode combination.

Other combinations of leads and electrodes are also commonly used with implantable programmable pacemakers in addition to the bipolar stimulation lead 42 shown in FIG. 3. The pacemaker 40 which is shown in FIG. 3 is a single chamber pacemaker adapted for pacing the right ventricle 48 with a bipolar stimulation lead 42. Unipolar pacing leads are also commonly used in the art, as are dual chamber pacemakers. A dual chamber pacemaker has a unipolar and/or bipolar pacing lead directed to the right atrium 50 as well as a unipolar and/or bipolar pacing lead directed to the right ventricle 48. All such pacemaker configurations are useable with the present invention. Therefore, the configuration shown in FIG. 3, and the other figures herein, is only exemplary.

Also shown in FIG. 3 is an external programmer 52. The programmer 52 is shown on one side of a schematically depicted layer of skin or flesh 51, while the pacemaker 40 and the heart 14 are shown on the other side, thereby symbolically representing the fact that the pacemaker 40 is implanted while the programmer 52 is external (non-implanted). The programmer 54 communicates with the implanted pacemaker 40 using any suitable communication link, such as through a radio frequency (RF) telemetry link, or through the use of other modulated electromagnetic fields. The communication link between the pacemaker 40 and the external programmer 52 is represented in FIG. 3 as a wavy line 54 which passes through the flesh 51.

It should be noted that the communication link 54 is bi-directional. That is, through this communication link 54, data is both sent to and received from the pacemaker 40 from the programmer 52. Data sent to the pacemaker 40 sets the parameters within the pacemaker 40 which control its operation. Further, through this communication link 54, data is sent from the pacemaker 40 to the programmer 52. Data from the pacemaker 40 includes information concerning sensed cardiac activity and status information relative to the operation of the pacemaker 40.

It is thus through this link 54 that the pacemaker 40 is "programmed" to operate in a desired fashion, including the manner required for the present invention. The manner of programming, and the various programming options available, for the wide variety of programmable pacemakers currently available is well known and documented in the art. See, e.g., U.S. Pat. No. 4,712,555, to Thornander et al., and U.S. Pat. No. 4,788,980, to Mann et al.

Figure 4:
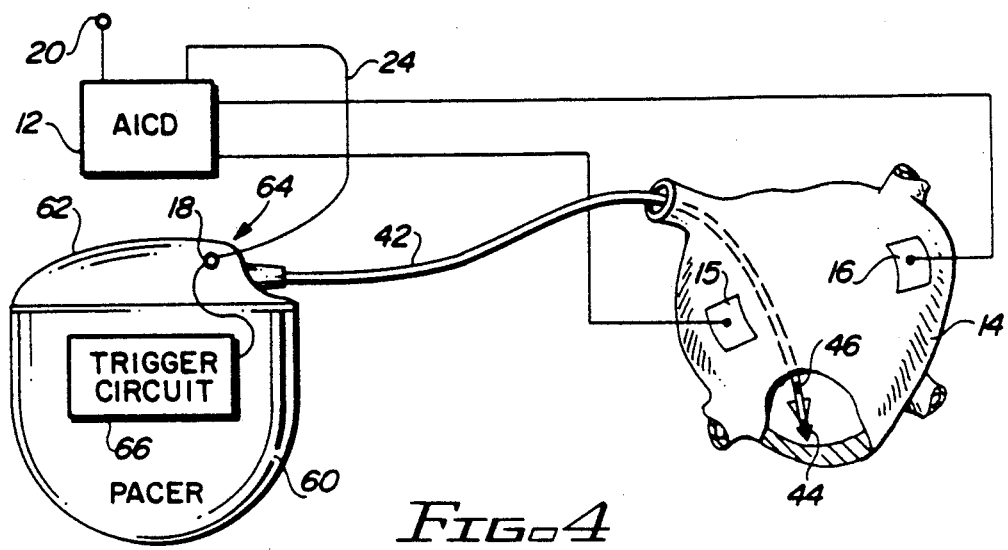
FIG. 4 is a pictorial representation of the AICD and pacemaker combination of the present invention.

Referring next to FIG. 4, a pictorial block diagram of one embodiment of the present invention is illustrated. The invention includes a modified programmable pacemaker 60 used in combination with an otherwise conventional AICD device 12. The AICD device 12 includes stimulating electrodes 15 and 16 in contact with the heart 14 as described previously in connection with FIG. 1. The pacemaker 60 includes a bipolar lead 42, having the tip electrode 44 and the ring electrode 46, positioned in a desired chamber of the heart 14, typically the right ventricle. (As has been previously indicated, and as is repeated here for emphasis, it is to be understood that this pacemaker 60/bipolar lead 42 configuration is only exemplary, since any type lead, bipolar or unipolar, could be used with any type pacemaker, dual or single chamber, to form part of the present invention.)

However, unlike prior art pacemakers, the modified pacemaker 60 includes a special connection port 64 which is included within the pacemaker connector 62. This port 64 is designed to receive the sense electrode 18 of the AICD device 12. A special trigger circuit 66 within the modified pacemaker 60 is electrically connected to the port 64, thereby making electrical contact with the sense electrode 18.

It should be noted that the other sensing electrode 20 of the AICD device 12 may continue to form part of the AICD case, or be placed near thereto, in which event the connection between the AICD device 12 and the pacemaker 60 is essentially a unipolar connection, as shown in FIG. 4. Alternatively, the electrode 20 may also be connected to the pacemaker connector 62, in which case a bipolar connection between the two devices would be established. The exact type of connection established between the AICD device 12 and the pacemaker 60 is unimportant for purposes of the present invention.

Figure 5:
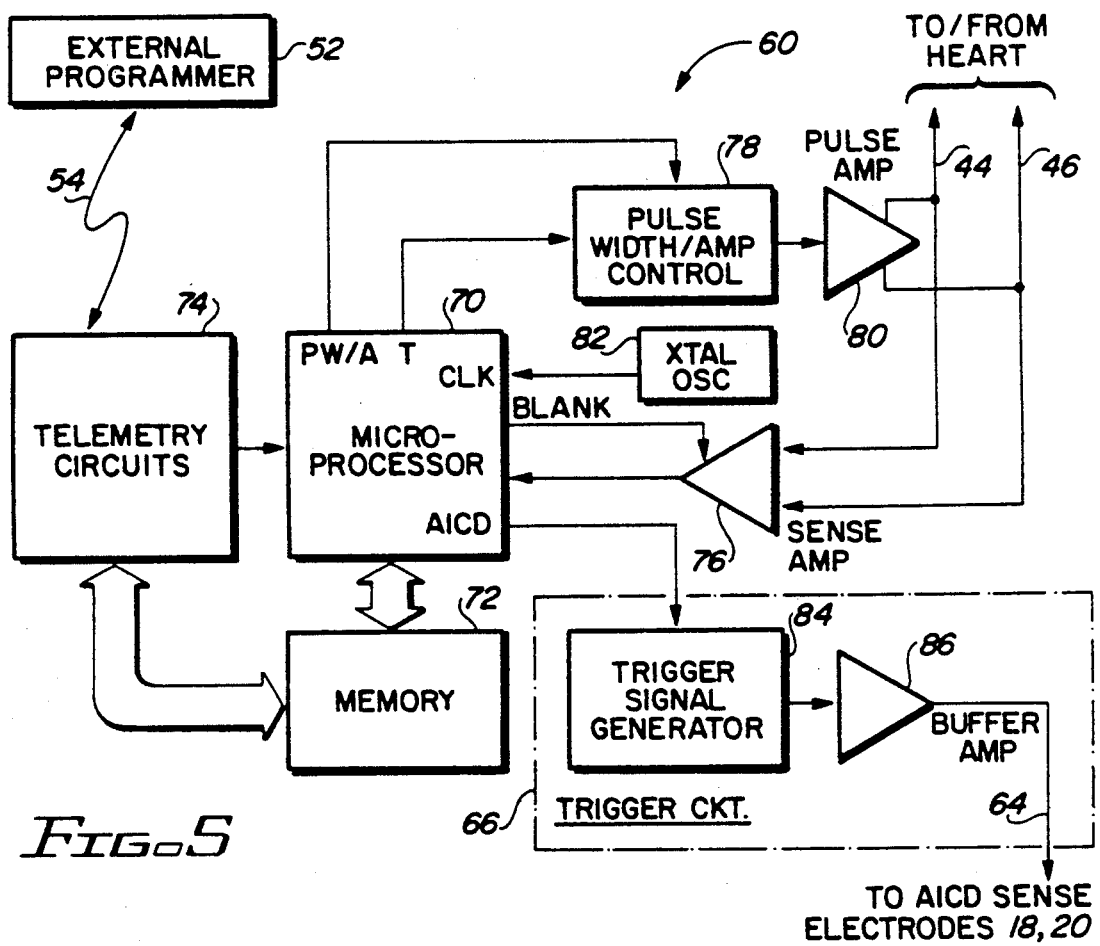
FIG. 5 is a functional block diagram of a programmable pacemaker modified for use with an AICD in accordance with the present invention.

FIG. 5 is a functional block diagram of the modified pacemaker 60 used with the present invention. This modified pacemaker 60 is essentially the same as conventional programmable pacemakers, but includes the addition of the trigger circuit 66 and the port 64. Further, as explained below, the operating programs stored in the pacemaker 60 are modified somewhat in order to accommodate the trigger circuit 66, or to make other contact with the AICD device 12.

As seen in FIG. 5, the pacemaker 60 includes, in addition to the trigger circuit 66, a microprocessor 70, a memory 72 which may be, for example, both ROM and RAM, telemetry circuits 74, a sense amplifier 76, a pulse width/amplitude control circuit 78, a pulse amplifier 80, and a crystal oscillator 82. These circuits and elements operate and cooperate with each other in a manner which is known and described in the art. Hence, only a brief overview of their operation is presented herein.

In operation, the microprocessor 70 controls the operation of the pacemaker 60 as determined by programs stored in the memory 72. Basic operating programs are resident in ROM, while most controlling parameters are programmed into RAM by way of the telemetry circuits 74, as received from the external programmer 52 over the communication link 54. Essentially, it is the basic function of the pacemaker 60 to provide stimulation pulses to the heart 14 (FIG. 4) on demand.

To this end, the sense amplifier 76, which has its input terminal coupled to the tip and ring electrodes 44 and 46, monitors the heart activity. When a heart beat is sensed (which heart beat appears as an electrical signal at the tip/ring electrodes 44 and 46), a signal is sent by the sense amplifier 76 to the microprocessor 70. If a heart beat is not sensed within a prescribed time period (typically referred to as an "escape interval"), the microprocessor sends a trigger pulse through the pulse width/amplitude control circuit 78 to the pulse amplifier 80, which delivers a stimulation pulse to the tip/ring electrodes 44 and 46.

The energy of the delivered stimulation pulse is set by the pulse width/amplitude control circuit 78, based on information programmed into the microprocessor 70 and the memory 72. The crystal oscillator 82 provides a basic clock signal for use by the microprocessor 70 upon which all timing measurements are based. While a stimulation pulse is being delivered to the heart by the pulse amplifier 80, and for a prescribed period of time thereafter, the sense amplifier 76 is effectively turned off by a blanking signal received from the microprocessor 70.

As will be evident to those skilled in the art, the above description of the pacemaker 60 and its operation is a functional description. As such, the exact circuits which may be used by a particular programmable pacemaker in order to achieve the described function may differ significantly from the description given. For example, not all programmable pacemakers employ a microprocessor, as suggested in FIG. 5. Rather, many use dedicated circuitry which performs the same function as the microprocessor. Any and all of these pacemaker variations could, however, be successfully employed as part of the present invention.

Further, it is noted that many modern pacemakers advantageously include means for not only sensing when the heart is contracting within a prescribed escape interval, but also for determining whether the heart is beating too fast (tachycardia) or too slow (bradycardia). In such a case, attempts are made by the pacemaker to break the tachycardia or bradycardia condition by delivering a prescribed sequence or pattern of stimulation pulses. See, for example, above-referenced U.S. Pat. No. 4,788,980, to Mann et al., which patent is hereby incorporated herein by reference.

However, disadvantageously, such attempts by the pacemaker to break the tachycardia or bradycardia may not be successful. In such an instance, the combination of the present invention may selectively and programmably step in and further attempt to break the detected condition (e.g., tachycardia) by causing a higher energy stimulation pulse to be delivered to the heart whenever selected programmed criteria have been detected.

Still referring to FIG. 5, it may be seen that the trigger circuit 66 need only include a trigger signal generator 84 and a buffer amplifier 86. The purpose of the trigger signal generator 84 is simply to convert a logic signal generated by the microprocessor 70, labeled AICD in FIG. 5, into a pulse or trigger signal which is capable of being sensed by the AICD device 12 through its sense electrode 18 as a signal indicating that a high energy stimulation pulse or pulses should be generated. In this respect, it is noted that in the case of a sensed bradycardia, it is the absence of a signal on sensing electrode 18 which triggers the generation of a high energy stimulation pulse(s) by the AICD device 12.

Hence, in the case of a sensed bradycardia, it is the function of the trigger signal generator 84 to suppress any signals from being sent to the AICD device through its sensing electrode 18. However, in the case of a sensed tachycardia, particularly a tachycardia as defined by a programmable threshold within the pacemaker, it is the function of the trigger signal generator 84 to convert the logic signal which identifies the tachycardia condition into a series of pulses which will be interpreted by the AICD device as a heart rate which exceeds its fixed rate threshold. At all other times, e.g., when the heart rate is sensed as being "normal", it is the function of the trigger signal generator 84 to convert the logic signal which identifies an acceptable heart rate into a series of pulses which will be interpreted by the AICD device as a normal heart rate.

The buffer amplifier 86 of the trigger circuit 66 amplifies and buffers the trigger pulse signals from the trigger signal generator 84 in such a manner so that the signals appear to the AICD device 12 as though they originated at the heart 14 or other tissue location where the sense electrode 18 is positioned. Any suitable operational amplifier, or equivalent, may be configured by those skilled in the art to serve this function.

Those skilled in the art will recognize that the function performed by the trigger signal generator 84 and the buffer amplifier 86 could be performed through suitable programming of the microprocessor 70. Accordingly, variations of the present invention may have the trigger circuit 66 implemented entirely in software or firmware (i.e., in the controlling programs) associated with the microprocessor 70.

Figure 8:
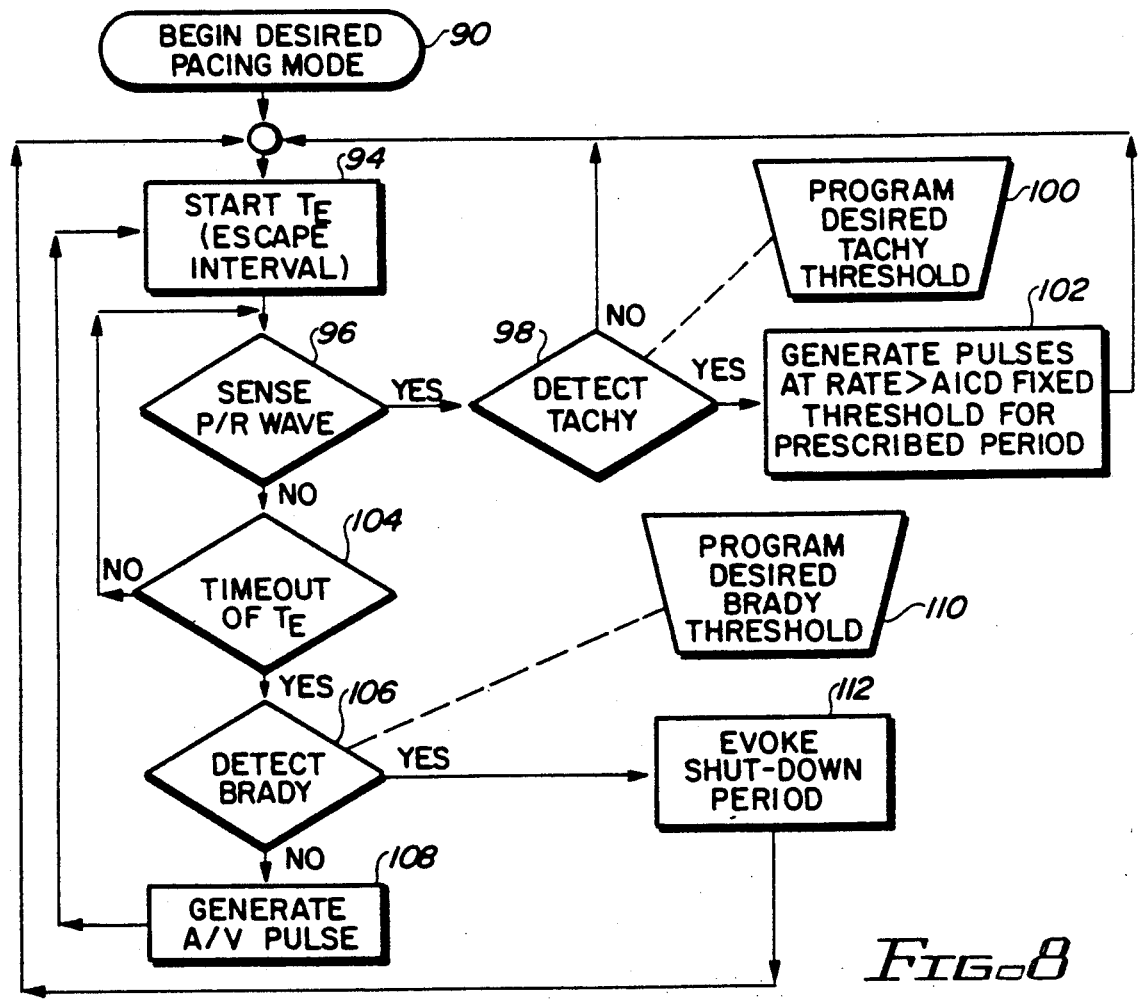
FIG. 8 is a flow chart of a basic program used within a modified pacemaker of the present invention intended for use with a conventional AICD device.

Referring next to FIG. 8, a flow chart is illustrated which indicates the basic program or manner in which the modified pacemaker 60 of FIG. 5 operates. Only the operation as it relates to the present invention is shown. Other pacemaker features, although included in most modern demand pacemakers, but having no impact on the present invention, are omitted for clarity. FIG. 8 assumes that a desired pacing mode has been initiated (block 90). The type of pacing mode, such as, for example, VVI, DDI, AVI, etc., is unimportant for purposes of the present discussion.

Once in the desired pacing mode, the escape interval is then started (block 94), and the sense circuits of the pacemaker are allowed to monitor heart activity (block 96) to determine if a P-wave (indicating a contraction of the atrium) or an R-wave (indicating a contraction of the ventricle) occurs. If so, that is, if a P/R-wave is sensed before the escape interval times out, then a determination is made as to whether a tachycardia is present (block 98). If not, then control returns to block 94, and the process repeats, i.e., the escape interval is reset (restarted).

The decision made at block 98 as to whether a tachycardia is sensed is carried out in conventional manner, and typically requires monitoring the heart 14 (FIG. 4) for more than one cardiac cycle. Advantageously, however, this decision may be based on programmable thresholds (block 100) which are programmed into the pacemaker, not the fixed threshold which is built into the AICD device.

If a decision is made at decision block 98 that a tachycardia condition exists, then appropriate trigger pulses are generated (block 102) at a rate which exceeds the fixed rate threshold of the AICD device. These pulses are presented to the sense electrode 18 of the AICD device, as above described, and are interpreted by the AICD device to be a heart beating at a rate exceeding the fixed threshold. Hence, the high energy stimulation pulse(s) are evoked by the AICD device in an attempt to break the sensed tachycardia. This process repeats as often as is necessary to break the tachycardia.

If a P/R-wave is not sensed at decision block 96, then monitoring of heart activity continues for the remainder of the escape interval (block 104). If the escape interval times out without having detected a P/R wave, then a decision is made (block 106) as to whether a bradycardia condition is present. If not, an atrial (A) or ventricular (V) stimulation pulse is generated (block 108) in conventional demand pacemaker fashion. Control returns to block 94, where the escape interval is reset and the process repeats.

If a decision is made at decision block 106 that a bradycardia condition exists (which decision may be made in conventional manner, but advantageously using programmed criteria (block 110), not the non-programmable low rate threshold associated with the AICD device, then a shut-down period is evoked (block 112) during which no trigger pulses are generated by the trigger circuit 66. This shut-down period advantageously assures that the sense electrode 18 of the AICD device 12 will not sense any cardiac activity for the prescribed activity, thereby assuring that a high energy stimulation pulse(s) will be generated by the AICD device, which high energy stimulation pulse(s) will hopefully break the bradycardia or successfully defibrillate the heart.

It should be noted that for purposes of the present discussion, a bradycardia condition and a fibrillation condition are sensed and treated in the same way. That is, a fibrillating or stopped heart is treated by the invention in the same manner as a heart which is beating too slow.

It may be noted that the above description relating to FIGS. 4, 5, and 8 relates generally to a first embodiment of the present invention wherein the sensing electrode 18 of the AICD device 12 is connected directly to the pacemaker 60. A second embodiment of the invention contemplates no direct electrical connection between the AICD device 12 and the pacemaker 60, but rather utilizes an indirect connection. This indirect connection is achieved between the sensing electrodes 18 and 20 of the AICD device and the tip and ring electrodes 44 and 46 of the pacing lead 42 of the pacemaker 60.

A pictorial representation of the components of this second embodiment would simply be the combination of FIGS. 1 and 3. That is, an AICD device 12 would be coupled to the heart 14 in conventional manner, as would a pacemaker 40. However, the pacemaker 40 would be modified, particularly in the programs stored therein, in order to complete the indirect coupling between the two devices.

In accordance with this second embodiment, the pacemaker 40, upon sensing a tachycardia or bradycardia condition, generates a series or sequence of low energy pulses, having insufficient energy to stimulate the heart, but having sufficient energy to be detected by the sense electrodes and circuits of the AICD device 12. In practice, such low energy pulses may be realized by using narrow pulses of a convenient amplitude. Such low energy pulses may be thought of as a code, appearing at the tip/ring electrodes 44 and 46, which code is sensed by the sensing circuits of the AICD device 12.

Figure 6:
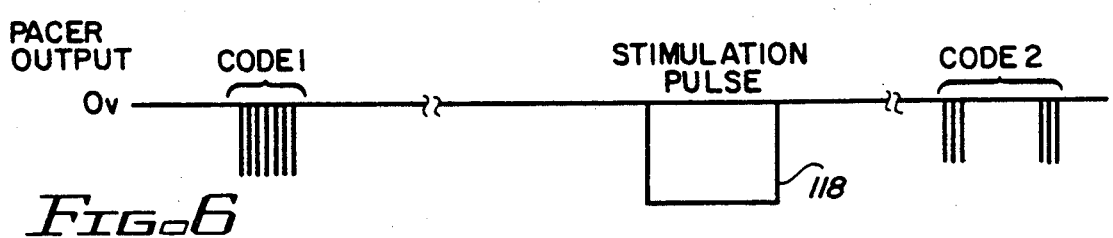
FIG. 6 is a waveform diagram illustrating two exemplary pulse codes which may be used with the modified pacemaker of at least one embodiment of the present invention to signal the AICD device that a prescribed heart condition has been sensed and that one or more high energy stimulation pulses are needed.

Exemplary codes which could be used are illustrated in FIG. 6, where two such codes, identified as Code 1 and Code 2, are shown. Also included in FIG. 6 is a typical stimulation pulse 118. This stimulation pulse 118 is much wider than the narrow pulses included in pulse Codes 1 and 2, and thereby has much more energy associated therewith. The pulse codes are deliberately made very narrow, on the order of a few microseconds, for example, 10-30 microseconds, whereas a typical stimulation pulse may be 2-5 milliseconds in width in order to prevent the pulse codes from actually stimulating the heart tissue.

The amplitudes of the pulse codes shown in FIG. 6 are roughly the same as that of the stimulation pulse, which is typically 3-5 volts. However, this is only exemplary, and any suitable amplitude which can be sensed may be used. In practice, only a limited range of amplitudes are readily available within a pacemaker device, typically in the range of 2.8 volts to 10 volts.

Figure 7A:
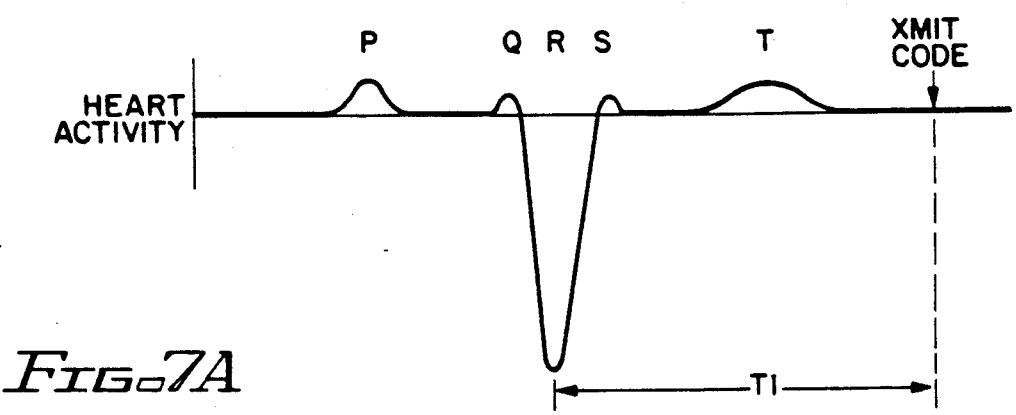
FIG. 7A depicts a typical ECG waveform illustrating the P-QRS-T cycle of the heart as sensed by the sensing circuits of the pacemaker, and further illustrates one possible timing relationship which may be used to transmit a desired pulse code in synchronism with the heart cycle.
Figure 7B:
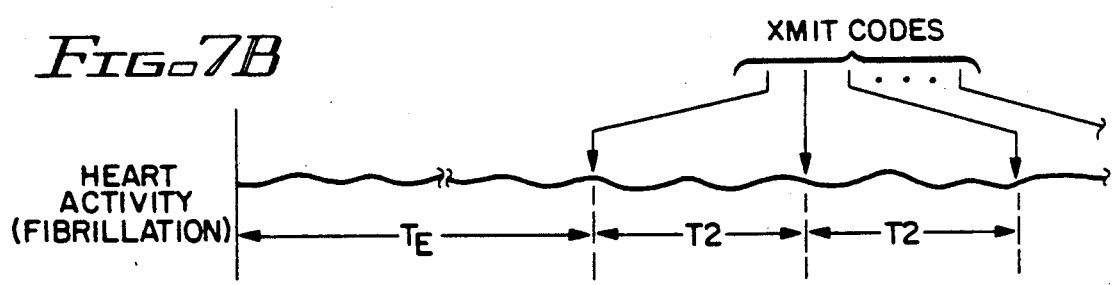
FIG. 7B depicts an ECG waveform for a fibrillating heart, and also illustrates one possible timing relationship which may be used to transmit a fibrillation pulse code.

Referring next to FIGS. 7A and 7B, some typical cardiac waveforms are illustrated. FIG. 7A shows a conventional P-QRS-T cardiac cycle which occurs in a normally beating heart. FIG. 7B shows a cardiac cycle for a heart which is in fibrillation (not beating). These waveforms are shown for the purpose of illustrating a preferred timing relationship relative to the cardiac cycle during which the pulse codes may be transmitted.

The waveform illustrated in FIG. 7A is for a single cycle. If the heart 14 (FIG. 3) is beating normally, the cycle repeats for each heart beat. The time between successive R-waves represents the period of the heart beat frequency. For a typical heart beating at 70 beats per minute, this period is approximately 860 milliseconds. Thus, there is roughly 860 milliseconds between successive R-waves. The time separating the P-wave from the R-wave may be on the order of 50-120 milliseconds. Hence, there is usually at least 700 milliseconds between an R-wave and the next P-wave. However, these times change as the heart rate changes, with faster heart rates having correspondingly shorter time periods.

For purposes of the second embodiment of the present invention, it is desirable that the pulse code not be transmitted at a time during the cardiac cycle when the pulse code will not be detectable or when it might otherwise cause problems. This means that it should not be transmitted coincident with either the P-wave or the R-wave. Further, it is desirable not to transmit any stimulation pulses during repolarization of the heart tissue (i.e., during the T-wave portion of the cycle), even if these pulses are of insufficient energy to stimulate the heart tissue.

Therefore, it is necessary to synchronize the delivery of the pulse code with the cardiac cycle. The preferred approach for achieving such synchronization is to wait a time T1 after the R-wave before transmitting a pulse code, as shown in FIG. 7A. The time T1 is selected to be long enough to ensure that the T-wave has terminated, but also short enough to be prior to the next P-wave. Values for T1 on the order of 200-300 milliseconds would generally meet these criteria, although these times could be adjusted to be somewhat shorter for a tachycardia condition, and to be significantly longer for a bradycardia condition. The existing circuits within the pacemaker 60 may be easily modified, typically through merely reprogramming, to allow low stimulation pulses to be generated at any selected time after a synchronizing event, such as the occurrence of an R-wave.

In FIG. 7B, where a fibrillating heart condition exists, the timing of the pulse code, for example, Pulse Code 2 (used to signal a fibrillation condition), is not important. A fibrillating heart is essentially a stopped heart, and there are no cardiac events from which synchronization may be obtained. Accordingly, the preferred approach is to generate the appropriate pulse code at the end of the escape interval, $T_E$, (or alternatively, at the end of two or three escape intervals) and to repeat the pulse code every T2 seconds thereafter.

If the heart starts beating, as a result of the AICD device transmitting a high energy defibrillation pulse in response to sensing the pulse code, or in response to not sensing any cardiac activity, then the repeating pulse codes will do no harm. After a suitable time period, once the heart is again beating at a normal rate, transmission of this code sequence may be terminated.

Figure 9:
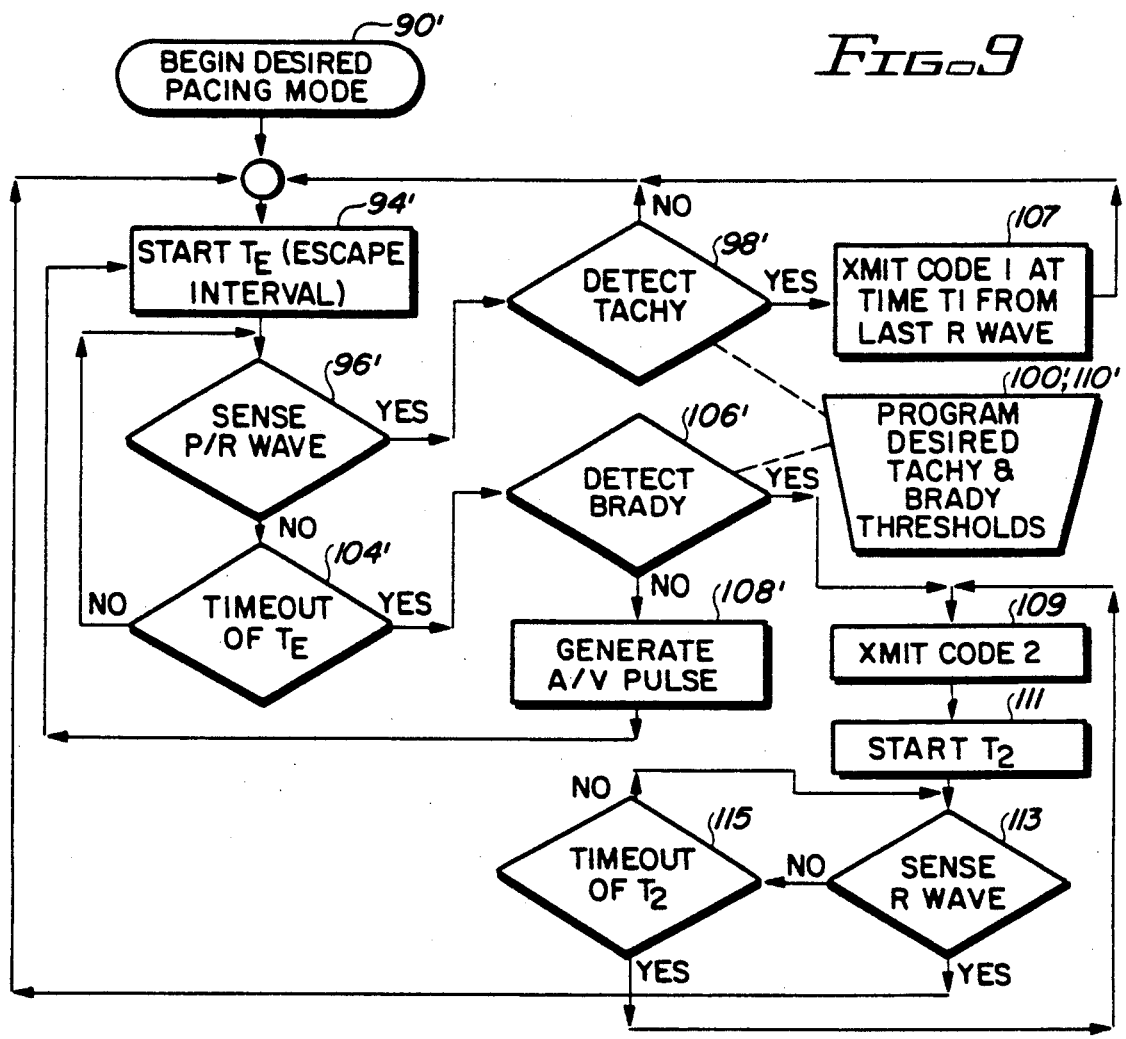
FIG. 9 is a flow chart of an alternative program used within a modified pacemaker of the present invention intended for use with a modified AICD device.

FIG. 9 is a basic flow chart of the program which could be implemented in the pacemaker with this second embodiment. This flow chart is very similar to the flow chart of FIG. 8, particularly the upper half thereof. Equivalent steps or blocks in the flow chart of FIG. 9 relative to the flow chart of FIG. 8 are therefore labeled with the same numbers, except for the addition of a "prime" symbol (') after the number in FIG. 9. Accordingly, much of the explanation given above in connection with FIG. 8 applies equally well to FIG. 9, and will not be repeated here.

The main difference between the program illustrated in FIG. 9 over that shown in FIG. 8 is the actions taken in response to a determination that a tachycardia condition exists (block 98'), or a bradycardia condition exists (block 106'). If a tachycardia condition is sensed (block 98'), the appropriate pulse code corresponding to such determination, for example, Code 1, is generated at time T1 from the last R-wave (block 107), as described above in connection with FIG. 7A.

Similarly, if a bradycardia condition is sensed (block 106'), the appropriate pulse code corresponding to such determination, for example, Code 2, is generated (block 109), and that generation is repeated every T2 seconds (block 111), as described above in connection with FIG. 7B. If an R-wave is sensed during the T2 period (block 113), then normal demand pacemaker operation is reinitiated (block 94'). If the time interval T2 times out prior to detecting an R-wave (block 115), then Code 2 is transmitted again (block 109), and the process repeats until an R-wave is detected.

Because an AICD device usually contains means for sensing fibrillation (no heart beat), which sensing means will usually also sense a very slow heart beat (which it also interprets as no heart beat, because no heart beat is sensed within a prescribed time interval), and further because the AICD responds to such sensing by delivering a high energy defibrillation pulse, one might well ask what is the need of the present invention relative to programming the lower limit of the AICD device. In other words, it could be argued that for most patients the fixed lower limit of the AICD device is adequate, needing no programming.

However, for the first embodiment of the present invention, the sensing electrode of the AICD will not sense a fibrillation condition (or any other condition) because the sensing electrode is not in contact with the heart. It is in contact with the pacemaker; and it is only able to sense what the pacemaker allows it to sense. Therefore, programming both the upper and lower limits of the AICD is required, and indeed is included in the preferred embodiment.

For the second embodiment of the present invention, the AICD sensing electrode is in contact with the heart and is therefore sensing cardiac activity. Thus, all that the pacemaker need do to signal the AICD that a tachycardia has been sensed (as determined by its programmed thresholds, not the fixed threshold of the AICD) is to inject sufficient pulses into the cardiac cycle so that the combination of the natural heart activity and the injected pulses appears to the AICD sense circuits as a heart rate which exceeds its fixed tachycardia threshold.

In this regard, it would be sufficient for the pacemaker to inject any pulse code, including a single low energy stimulation pulse, at appropriate times in the cardiac cycle, in order to give the appearance to the AICD that the heart rate has exceeded the fixed upper threshold. Further, doing so would allow a conventional AICD device, having no special discrimination circuits therein, to be used with this second embodiment of the invention.

However, using a conventional AICD for this second embodiment is viewed as undesirable (unless an AICD is used only for the purpose of providing tachycardia support) because only the upper rate limit of the AICD could be effectively controlled. This is true since at or near the lower limit of the AICD, the demand pacemaker is stimulating the heart in an attempt to get it to beat at the programmed rate. These stimulation pulses will disadvantageously be interpreted by the AICD sensing circuits as cardiac activity. Thus, even though the heart may be experiencing a bradycardia condition or, worse yet, a fibrillation condition, the AICD will not sense this fact because of the presence of the stimulation pulses generated by the pacemaker at a programmed rate (in accordance with conventional demand pacemaker operation), which stimulation pulses are interpreted by the AICD as a beating heart.

Accordingly, it is not recommended that the second embodiment of the present invention be used unless special pulse codes are transmitted by the pacemaker so that they may be properly interpreted by the AICD sensing circuits. Otherwise, the AICD may be rendered ineffective at performing its most critical function—delivering a defibrillation pulse to defibrillate a fibrillating heart.

Figure 10:
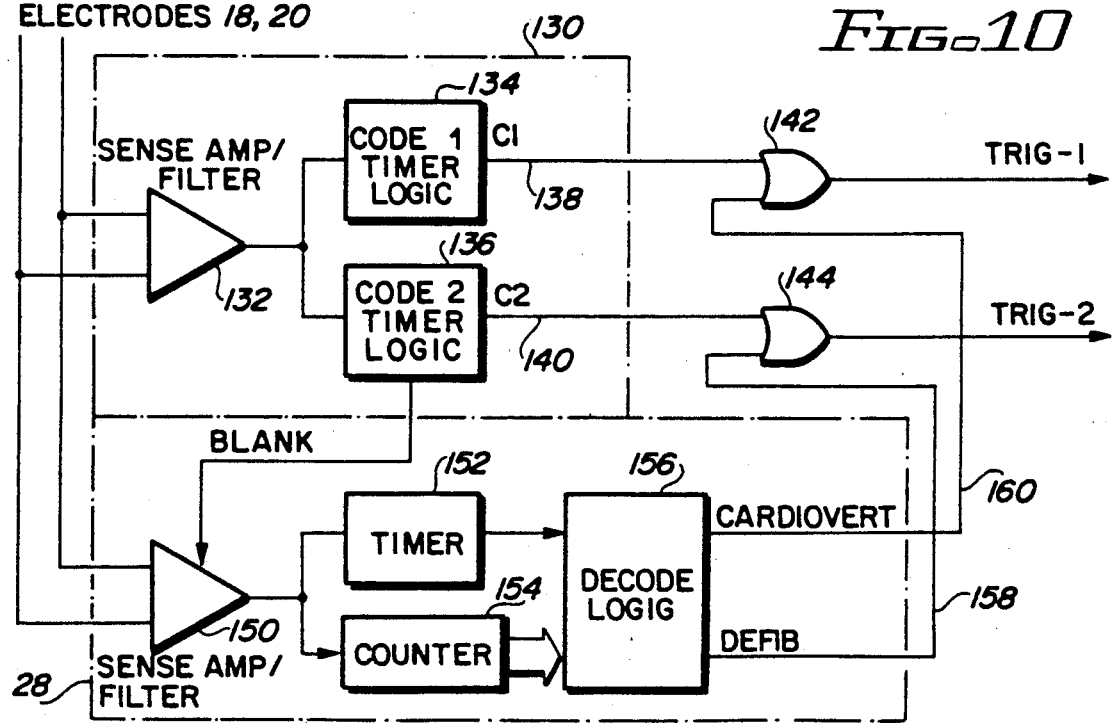
FIG. 10 is a block diagram of the modified AICD device of FIG. 10.

The use of pulse codes with the second embodiment requires that the sensing circuits of the AICD be modified in order to allow these sensing circuits to detect the pulse codes and distinguish them from other sensed activity, whether such activity comprises natural cardiac events, or normal stimulation pulses generated by the demand pacemaker. FIG. 10 illustrates a functional diagram of one technique in which such sensing circuits may be modified. In FIG. 10, it may be seen that the basic threshold circuits 28 (FIG. 2) of a conventional AICD device 12 have been modified to include a discrimination circuit 130.

The basic threshold circuit 28 typically includes a sense amplifier 150, a decode timer 152, a counter 154, and a decode logic 156. The sensing of any activity by the sense amplifier 150, which may also include a filter, initiates a time period (which may be thought of as an escape interval). If this time period times out without being reset by a subsequent sensed event, then the decode logic generates a defibrillation ("D") trigger on a signal line 158. Further, all sensed events are counted in the counter 154 during this time period. If a prescribed number of such events are counted during this interval, then this count provides an indication that the heart is beating too fast, and the decode logic 156 generates a cardiovert ("C") trigger on the signal line 160.

The discrimination circuit 130 modifies the above-described operation by providing a means for sensing and distinguishing the receipt of a desired pulse code, such as Code 1 or Code 2. As seen in FIG. 10, the circuit 130 includes a sense amplifier 132, having a desired bandpass characteristic (so as to be able to detect the narrow pulse widths associated with the pulse codes). This sense amplifier 130 thus senses the pulse codes, amplifies and conditions them, and presents them for further processing to the logic circuits 134 and 136.

The logic circuit 134, identified in FIG. 10 as the Code 1 Timer and Logic Circuit, determines if the signal which has been sensed by the amplifier 132 corresponds to Code 1. If so, a C1 signal is generated and placed on the signal line 138. Similarly, the logic circuit 136, identified in FIG. 10 as the Code 2 Timer and Logic Circuit, determines if the signal which has been sensed by the amplifier 132 corresponds to Code 2. If so, a C2 signal is generated and placed on the signal line 140.

If, for example, Code 1 corresponds to a determination that a tachycardia condition has been sensed by the pacemaker, then the C1 signal is combined with the "C" trigger signal (on the signal line 160 from the basic threshold circuit 28) in the OR gate 142, the output of which is a TRIG-1 signal which is used to signal the AICD to generate an appropriate high energy cardioversion pulse.

Following this same example, if Code 2 corresponds to a determination that a bradycardia or fibrillation condition has been sensed, then a blank signal is sent from the logic circuit 136 to effectively disable or blank the sense amplifier 150, and the C2 signal is combined with the "D" trigger signal (on signal line 158) in OR gate 144, the output of which is a TRIG-2 signal which is used to signal the AICD to generate an appropriate high energy defibrillation pulse. The blanking of the sense amplifier 150 is done to prevent the AICD sense circuits from interpreting any pacemaker stimulation pulses (which are likely being applied to the heart during a Code 2 condition) as cardiac activity. Many alternative designs could be implemented in this regard to inhibit the sense circuits from falsely concluding that pacemaker stimulation pulses were cardiac activity.

As above described, it may thus be seen that the present invention advantageously allows a non-programmable AICD device to be combined with a programmable pacemaker in a way which transfers the flexible programming features of the pacemaker to the inflexible AICD, thereby allowing the AICD/pacemaker combination to efficiently and programmably serve both the pacemaker and AICD functions.

Although exemplary embodiments of the present invention have been shown and described above, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention. Accordingly, the true scope of the invention should be determined with reference to the claims.

What is claimed is:

1. A programmable cardioverter/defibrillator system comprising:
   (a) an automatic implantable cardioverter/ defibrillator (AICD), said AICD comprising:
     high/low rate sensing means for sensing when a heart is beating above a fixed high threshold rate or below a fixed low threshold rate; and
     means for delivering a high energy cardioversion/defibrillation pulse to the heart whenever said high/low rate sensing means senses that the heart is beating above the fixed high threshold rate or below the fixed low threshold rate;
   (b) an implantable programmable pacemaker, said pacemaker comprising:
     heart-rate sensing means for sensing the rate at which the heart is beating;
     means for processing the sensed heart rate to determine whether the sensed heart rate lies within a programmed range of acceptable heart rates and for triggering the generation of said cardioversion/defibrillation pulse from said AICD so that the fixed high and low threshold rates of said AICD are replaced by the programmed range of heart rates of said implantable programmable pacemaker, said triggering occurring whenever the heart rate sensed by said heart rate sensing means of said pacemaker does not fall within said prescribed range of acceptable heart rates; and
     programming means for allowing said programmed range of acceptable heart rates to be programmed into said processing means; and
   (c) coupling means for coupling the operation of said AICD to said pacemaker.

2. The programmable cardioverter/defibrillator system of claim 1, wherein said coupling means comprises a direct electrical connection between said processing means of said pacemaker and said high/low rate sensing means of said AICD.

3. The programmable cardioverter/defibrillator system of claim 2, wherein said high/low rate sensing means of said AICD comprises a sensing electrode, and wherein said processing means of said pacemaker comprises a trigger circuit, and wherein said direct electrical connection is made between said trigger circuit and said sensing electrode.

4. The programmable cardioverter/defibrillator system of claim 3, wherein said trigger circuit comprises:
   means for generating a first series of pulses at a rate which exceeds the fixed high threshold rate of said high/low rate sensing means when said processing means of said pacemaker determines that the sensed heart rate exceeds the programmed range of acceptable heart rates, whereby said high/low rate sensing means of said AICD senses said first series of pulses and interprets said first series of pulses as a heart rate which exceeds the fixed high threshold rate of the AICD, thereby delivering said high energy cardioversion/defibrillation pulse to the heart.

5. The programmable cardioverter/defibrillator system of claim 4, wherein said pacemaker further comprises:
   means for delivering low energy stimulation pulses to the heart on demand in order to assist the heart in beating at a rate which is at least a programmed rate, and wherein said processing means of said pacemaker is programmed to deliver through said delivery means a first sequence of low energy pulses to the heart according to a first prescribed pattern upon the sensing of a fast heart rate by said heart-rate sensing means, said fast heart rate indicating a tachycardia condition, said first sequence of pulses being designed to break said tachycardia condition and cause the heart to beat at a slower rate, said processing means being further programmed to have said AICD deliver said high energy cardioversion/defibrillation pulse only in the event that said first sequence of low energy pulses generated by said pacemaker is unable to break said tachycardia condition.

6. The programmable cardioverter/defibrillator system of claim 3, wherein said trigger circuit comprises:
   means for inhibiting the generation of any pulses for a prescribed period of time when said processing means of said pacemaker determines that the sensed heart rate is less than the programmed range of acceptable heart rates, whereby said high/low rate sensing means of said AICD fails to sense any heart rate within said prescribed period of time and interprets the same as a heart rate which is below the fixed low threshold rate of the AICD, thereby delivering said high energy cardioversion/defibrillation pulse to the heart.

7. The programmable cardioverter/defibrillator system of claim 6, wherein said pacemaker further comprises:
   means for delivering low energy stimulation pulses to the heart on demand in order to assist the heart in beating at a rate which is at least a programmed rate, wherein said processing means of said pacemaker is programmed to deliver through said delivery means a sequence of low energy pulses to the heart according to a prescribed pattern upon the sensing of a slow heart rate by said heart-rate sensing means, said slow heart rate indicating a bradycardia condition, said sequence of pulses being designed to stop said bradycardia condition and cause the heart to beat at a faster rate, said processing means being further programmed to have said AICD deliver said high energy cardioversion/defibrillation pulse only in the event that said sequence of low energy pulses generated by said pacemaker is unable to stop said bradycardia condition.

8. The programmable cardioverter/defibrillator system of claim 1, wherein said pacemaker further comprises:
   means for generating and delivering low energy stimulation pulses to the heart on demand in order to assist the heart in beating at a rate which is at least a programmed rate, wherein said coupling means comprises very low energy stimulation pulses of a specified energy generated by said pulse generating means of said pacemaker, delivered to the heart, and sensed by said high/low rate sensing means of said AICD, the specified energy of said low energy stimulation pulses being insufficient to stimulate the heart.

9. The programmable cardioverter/defibrillator system of claim 8, wherein said processing means of said pacemaker is further programmed to generate a first code sequence of said very low energy pulses when said processing means determines that the sensed heart rate is above said programmed range of acceptable heart rates, and a second code sequence of said very low energy pulses when said processing means determines that the sensed heart rate is below said programmed range of acceptable heart rates, wherein said AICD high/low rate sensing means further comprises means for sensing said first and second code sequences and discriminating therebetween.

10. A programmable implantable medical system for delivering high energy stimulation pulses to a heart whenever the heart rate exceeds a programmable threshold rate value, said system comprising:
an automatic implantable cardioverter/defibrillator (AICD) device, said AICD device comprising:
AICD sensing means for sensing when a heart rate is above a fixed high threshold rate value; and
means for delivering a high energy stimulation pulse to the heart whenever said AICD sensing means senses that the heart rate exceeds said fixed high threshold rate value; and
an implantable pacemaker device, said pacemaker device comprising:
pacemaker sensing means for sensing the heart rate;
means for processing the sensed heart rate to determine if it exceeds programmed criteria;
programming means for programming said specified criteria into said processing means; and
means for generating and delivering a sequence of very low energy pulses to the heart at a rate which exceeds the AICD fixed threshold rate in response to a determination by said processing means that the heart rate exceeds said programmed criteria, said very low energy pulses having an energy level sufficient to be detected by the AICD sensing means, but insufficient to stimulate the heart, said sequence of very low energy pulses being detectable by the AICD sensing means, whereby said delivery means of said AICD device responds by delivering said high energy stimulation pulse to the heart.

11. The programmable implantable medical system of claim 10, wherein said AICD sensing means of said AICD device further comprises:
means for sensing when the heart rate is less than a fixed low threshold rate value, and wherein said delivery means comprises:
means for delivering a high energy stimulation pulse to the heart whenever said AICD sensing means senses that the heart rate is less than said fixed low threshold rate value, whereby said AICD device delivers a high energy stimulation pulse to the heart whenever the AICD sensing means senses that the heart rate is less than the fixed low threshold rate value, and whenever the pacemaker heart rate sensing means senses that the heart rate exceeds said programmed criteria.

12. The programmable implantable medical system of claim 11, wherein the programmed criteria of said implantable pacemaker device comprises:
a heart upper rate limit, said upper rate limit comprising a heart rate value above which an undesirable heart condition is deemed to exist, said upper rate limit comprising a programmable value which is less than the fixed high threshold rate value of said AICD device.

13. In combination, an automatic implantable cardioverter/defibrillator (AICD) device and an implantable programmable pacemaker device, said pacemaker device comprising:
heart-rate sensing means for sensing the rate at which the heart is beating;
means for processing the sensed heart rate to determine whether said heart rate is within a specified range of acceptable heart rates;
programming means for allowing said specified range to be programmed into said processing means; and
signaling means within said pacemaker device for sending a trigger signal to said AICD device upon a determination by said processing means that the sensed heart rate is not within said specified range of acceptable heart rates;
said AICD device comprising:
AICD sensing means for sensing when a heart is beating above a fixed high threshold rate or below a fixed low threshold rate;
means for delivering a high energy stimulation pulse to the heart in response to receiving said trigger signal or in response to said AICD sensing means sensing that the heart is beating above the fixed high threshold rate or below the fixed low threshold rate; and
receiving means within said AICD device for receiving said trigger signal;
said trigger signal sent by said signaling means comprising a series of pulses having a frequency at least as great as said fixed high threshold rate of said AICD device, said series of pulses being sent directly to said AICD receiving means when the heart rate sensed by said heart-rate sensing means of said pacemaker is above said specified range of acceptable heart rates; and
said trigger signal comprising an inhibiting of all pulses sent directly to the AICD receiving means for a prescribed period of time when the heart rate sensed by said heart-rate sensing means of said pacemaker is below said specified range of acceptable heart rates.

14. The combination of claim 13 wherein said signal means of said pacemaker comprises a trigger circuit which generates or inhibits said series of pulses, and wherein said receiving means of said AICD device comprises a sensing electrode coupled to the AICD sensing means, and further wherein said sensing electrode is electrically connected to said trigger circuit by means of a direct electrical connection.

15. A method of converting fixed high or low rate threshold values of an automatic implantable cardioverter/defibrillator (AICD) device to programmable high or low rate threshold values, said AICD including means for generating a high energy cardioversion/defibrillation pulse whenever the heart rate sensed by sensing means within said AICD device either exceeds the fixed high rate threshold value or is less than the fixed low rate threshold value, said method comprising the steps of:

coupling a programmable pacemaker to said AICD device by way of a direct electrical connection between a sensing electrode of said AICD device and a trigger circuit of said pacemaker, said pacemaker further including heart rate sensing means for sensing when the heart rate exceeds a programmable upper limit and is less than a programmable lower limit; and triggering the generation of said high energy cardioversion/defibrillation pulse whenever the heart rate sensing means of said pacemaker senses a rate which exceeds the programmable upper limit or is less than the programmable lower limit.

16. A method of converting fixed high or low rate threshold values of an automatic implantable cardioverter/defibrillator (AICD) device to programmable high or low rate threshold values, said AICD including means for generating a high energy cardioversion/defibrillation pulse whenever the heart rate sensed by sensing means within said AICD device either exceeds the fixed high rate threshold value or is less than the fixed low rate threshold value, said method comprising the steps of:

coupling a programmable pacemaker to said AICD device, said pacemaker including heart rate sensing means for sensing when the heart rate exceeds a programmable upper limit and is less than a programmable lower limit; and triggering the generation of said high energy cardioversion/defibrillation pulse whenever the heart rate sensing means of said pacemaker senses a rate which exceeds the programmable upper limit or is less than the programmable lower limit;

said coupling step comprising:

generating a low energy pulse within said pacemaker, said low energy pulse having insufficient energy to stimulate the heart, but sufficient energy to be sensed by the sensing means of said AICD device;

applying said low energy pulse to said heart at a rate that exceeds said fixed high rate threshold; and detecting the presence of said low energy pulse within the sensing circuits of said AICD.

17. In combination, an automatic implantable cardioverter/defibrillator (AICD) device and an implantable programmable pacemaker device, said pacemaker device comprising:

heart-rate sensing means for sensing the rate at which the heart is beating;

means for processing the sensed heart rate to determine whether said heart rate is within a specified range of acceptable heart rates;

programming means for allowing said specified range to be programmed into said processing means; and signaling means within said pacemaker device for sending a trigger signal to said AICD device upon a determination by said processing means that the sensed heart rate is not within said specified range of acceptable heart rates;

means for generating and delivering low energy stimulation pulses as controlled by said processing means;

said AICD device comprising:

AICD sensing means for sensing when a heart is beating above a fixed high threshold rate or below a fixed low threshold rate;

means for delivering a high energy stimulation pulse to the heart in response to receiving said trigger signal or in response to said AICD sensing means sensing that the heart is beating above the fixed high threshold rate or below the fixed low threshold rate; and receiving means within said AICD device for receiving said trigger signal;

said signaling means of said pacemaker device comprising a series of very low energy pulses which are generated and delivered to the heart by said stimulation pulse delivery means of said pacemaker device at a rate which exceeds said fixed high threshold rate of said AICD sensing means, and wherein said receiving means within said AICD device comprises said AICD sensing means, said very low energy pulses having an energy level sufficient to be detected by said AICD sensing means, but insufficient to stimulate the heart, whereby said AICD sensing means senses the series of very low energy pulses and interprets the same to be the heart beating at a rate which exceeds said fixed high rate threshold, whereby said delivery means of said AICD device responds by delivering said high energy stimulation pulse to the heart.

18. The combination of claim 17 wherein said sensing means, processing means and pulse generation and delivery means included within said pacemaker device further comprise:

means for controlling the delivery of said very low energy stimulation pulses with the rhythm of the heart so that each pulse of said series of low energy pulses occurs within the beating cycle of the heart at a time which allows it to be detected by said AICD sensing means.

19. The combination of claim 17 wherein said trigger signal sent by said signaling means comprises one of a plurality of different burst patterns of said very low energy pulses which are generated and delivered to the heart by said pulse generation and delivery means of said pacemaker device, and further wherein said receiving means within said AICD device includes discrimination means for discriminating between said different burst patterns, whereby each of said different burst patterns can be detected and identified by the receiving and discrimination means within said AICD device.

20. The combination of claim 19 wherein a first of said plurality of very low energy burst patterns signals that a heart rate lower than the specified range of acceptable heart rates programmed into said processing means has been sensed, and a second of said plurality of low energy burst patterns signals that a heart rate higher than the specified range of acceptable heart rates programmed into said processing means has been sensed.

* * * * *